US005612225A

United States Patent [19]
Baccanti et al.

[11] Patent Number: 5,612,225
[45] Date of Patent: Mar. 18, 1997

[54] PROCESS AND APPARATUS FOR DETERMINING TOTAL NITROGEN CONTENT BY ELEMENTAL ANALYSIS

[75] Inventors: Marco Baccanti, Milan; Paolo Magni, Besana in Brianza, both of Italy

[73] Assignee: Fisons Instruments S.p.A., Milan, Italy

[21] Appl. No.: 473,126

[22] Filed: Jun. 7, 1995

Related U.S. Application Data

[63] Continuation of Ser. No. 113,436, Aug. 27, 1993, abandoned.

[30] Foreign Application Priority Data

Aug. 31, 1992 [IT] Italy ................... MI92A2034

[51] Int. Cl.⁶ .................. G01N 31/12; G01N 33/00
[52] U.S. Cl. .................. 436/114; 436/52; 436/53; 436/106; 436/115; 436/155; 436/159; 436/160; 422/78; 422/80; 422/81; 422/89
[58] Field of Search .................. 422/78, 80, 81, 422/89, 95; 436/106, 114, 115, 155, 159, 160, 52, 53

[56] References Cited

U.S. PATENT DOCUMENTS

| | | | |
|---|---|---|---|
| 3,304,159 | 2/1967 | Hinsvark | 436/115 |
| 3,698,869 | 10/1972 | Condon | 436/115 |
| 3,877,875 | 4/1975 | Jones et al. | 436/114 X |
| 3,892,528 | 7/1975 | Fredericks | 436/114 X |
| 4,066,402 | 1/1978 | Komiyama et al. | 436/115 |
| 4,070,115 | 1/1978 | Fraim | 436/114 |
| 4,095,949 | 6/1978 | Flett | 436/114 |
| 4,234,315 | 11/1980 | Scott | 436/115 |
| 4,285,699 | 8/1981 | Itoh | 436/114 |
| 4,332,591 | 6/1982 | Oi et al. | 436/114 |
| 4,401,763 | 8/1983 | Itoh | 436/115 |
| 4,467,038 | 8/1984 | Scott | 422/80 X |
| 4,525,328 | 6/1985 | Bredeweg | 422/80 |
| 4,650,499 | 3/1987 | Scott | 422/80 X |

FOREIGN PATENT DOCUMENTS 1528032 6/1968 France.

OTHER PUBLICATIONS

R. Belcher et al. *Anal. Chim. Acta* 1968, 43, 441–450.
D. Povoledo *Chem. Abstr.* 1969, 70, 40567s.
K. Hozumi et al. *Microchem. J.* 1970, 15, 481–497.
R. Fiedler et al *Anal. Chim. Acta* 1973, 63, 435–443.
T. L. Lunder *Chem. Abstr.* 1974, 81, 11920y.
C. Starr et al. *Chem. Abstr.* 1984, 101, 226287a.
G. F. Adami et al. *Chem. Abstr.* 1986, 105, 111285c.

(List continued on next page.)

*Primary Examiner*—Arlen Soderquist
*Attorney, Agent, or Firm*—Millen, White, Zelano, & Branigan, P.C.

[57] ABSTRACT

This invention provides a process for determining the nitrogen content of a sample involving (a) combusting the sample in a combustion reactor in the presence of oxygen, which oxygen is introduced into the combustion reactor in pulse form; (b) reducing the resulting combustion gases by flowing them in a flow of helium or other noble carrier gas through a Cu-containing reduction reactor; (c) performing the steps of (i) making anhydrous in a water trap the reduced gases, (ii) flowing the reduced gases through a gas-chromatographic column in order to carry out a gas-chromatographic separation of $N_2$ from $CH_4$ possibly present within the reduced gases, and (iii) removing $CO_2$ from the reduced gases using a $CO_2$ trap, with the proviso that step (i) immediately precedes step (ii); and (d) analyzing the resulting gases by detecting thermal conductivity. This invention also provides an apparatus for determining the total nitrogen content of a sample which apparatus has a combustion reactor, a device for introducing oxygen into the combustion reactor in pulse form, a reduction reactor, a device for trapping water, a device for removing $CO_2$ from combustion and carrier gases, a thermal conductivity detector, and a gas chromatographic column upstream of the detector packed with a material suitable to separate nitrogen from methane possibly present within the combustion gases.

15 Claims, 4 Drawing Sheets

OTHER PUBLICATIONS

B. M. Schnitter et al. *J. Agric. Food Chem.* 1989, 37, 992–994.

R. Siegfried *Fresenius Z. Anal. Chem.* 1989, 335, 489–492.

J. Theobald *Chem. Abstr.* 1990, 113, 4742t.

E. Antonio et al. *Chem. Abstr.* 1990, 113, 96220x.

E. Pella *Chem. Abstr.* 1991, 114, 177608c.

G. K. Buckee Chem. Abstr. 1995, 122, 8290c.

G. K. Buckee *Monogr.–Eur. Brew. Conv.* 1993, 20, 2–13.

PROCESS AND APPARATUS FOR DETERMINING TOTAL NITROGEN CONTENT BY ELEMENTAL ANALYSIS

CROSS-REFERENCE TO RELATED APPLICATION

This application is a continuation of application Ser. No. 08/113,436, filed Aug. 27, 1993, now abandoned.

BACKGROUND OF THE INVENTION

1. Field of the Invention

The present invention concerns a process and an apparatus for determining the content of total nitrogen in a sample by means of combustion elemental analysis.

2. Description of the Prior Art

The classical method for the determination of total nitrogen and proteins in a sample is the one known as wet Kjeldahl method. This method is based on the digestion of the sample with concentrated $H_2SO_4$ and subsequent titration with ammonia. Though endowed with the outstanding advantage of enabling the analysis of samples in the order of 1–3 g, the Kjeldahl method has been recently more and more replaced by combustion methods, that allow a more simple process and its almost full automation.

The methods for combustion elemental analysis (or ultimate analysis) substantially provide to perform a flash dynamic combustion of small sample amounts in high excess of oxygen, in presence of catalysts, and the treatment of the thus obtained combustion gases by having them pass, under helium flow as carrier gas, successively through a copper-containing reduction reactor, a trap for $CO_2$ absorption, a trap for water absorption and a gas chromatographic column packed with an adsorbent (e.g. Porapack QS) that has the function of separating nitrogen from other combustion gases. The determination of nitrogen eventually takes place by means of a thermal conductivity detector and the function of the Porapack column, besides the aforesaid one, is also that of improving the shape of the $N_2$ peak and of providing the equipment with the necessary pneumatic resistance.

The major drawback of these methods is given by the fact that to obtain reliable results, only reduced amounts of samples, of about 10–20 mg, can be analyzed. Larger samples can be analyzed only if substantially deprived of organic compounds or with very reduced content thereof. This reduced capacity of analysis, as far as the sample quantity is concerned, leads to the need of homogenizing as accurately as possible (e.g. by grinding at liquid nitrogen temperature) the sample before drawing therefrom the portion to be analyzed, with all ensuing practical problems.

An attempt to solve said problems is given by the analytical method proposed by LECO company (USA). This method provides to perform a flash combustion of samples of 200–300 mg in $O_2$ flow, and to treat a reduced amount, corresponding to about 10% or less, of the gases coming out from the reactor and previously diluted with He, in a way similar to the one above disclosed, The drawbacks of this method are due to the sealing problems deriving from the extreme complexity of the equipment, to the fact that in any case only part of the gases is analyzed, and to the problems of homogenization of the gases themselves.

SUMMARY OF THE INVENTION

The aim of the present invention is therefore to make possible to determine total nitrogen content by means of combustion analysis of relatively large samples, of about 100–500 mg and up to 1.5–2.0 g, also in a fully automated way.

Said goal is achieved by means of the present invention that concerns a process for determining the nitrogen content of a sample, of the type comprising the combustion of said sample and subsequent reduction of the combustion gases by flowing them in a flow of helium or similar carrier gas through a Cu-containing reactor, characterized in comprising the following steps:

making anhydrous the gases coming out from said reduction reactor;

flowing said combustion gases through a gas chromatographic column, in order to carry out a gaschromatographic separation of $N_2$ from $CH_4$ possibly present in said combustion gases;

removing $CO_2$ from said gases in a $CO_2$ trap; and analyzing the thus treated combustion gases by means of a thermal conductivity detector.

The detector is kept at a temperature at least equal to that which permits the full vaporization of water present in said gases coming to the detector, namely at such a temperature as to maintain water under vapour form and simultaneously provide the detector with a sufficient sensitivity.

According to a preferred embodiment of the invention, the separation on chromatographic column is performed after gases are made anhydrous and before $CO_2$ is removed, and the gases coming out from the $CO_2$ removing means are fed directly to said detector.

According to another embodiment, $CO_2$ is removed at the same time of water, by means of anhydrous soda lime, before separation of $N_2$ from $CH_4$.

In this way it is possible to obtain a reliable and reproducible analysis, with minimal standard deviations, though operating on samples that weigh up to 1.5–2.0 g. In fact, thanks to the present invention, it is no longer necessary to perform the combustion in oxygen excess, since $CH_4$ possibly forming by pyrolysis during combustion is separated from nitrogen before performing detection by thermal conductivity. In fact, we found that according to known elemental analysis techniques no $CH_4$ was produced during flash combustion because of the small amount of sample and of the high oxygen excess. We also found that bad performances of those techniques were due to the fact that when larger amounts of sample are fed to combustion reactor, even if a large excess of oxygen is used, the pyrolisis gases cloud that is formed is such that there is no complete contact of this cloud with the oxygen and $CH_4$ is formed. Because of this methane formation no reliable results could be obtained when operating according to prior art techniques.

The specific arrangements of the $CO_2$ trap and the appropriate heating of the thermal conductivity detector (TCD) allow to overcome all problems resulting from the formation of large volumes of water in the $CO_2$ trap because of the high quantities of carbon dioxide resulting from the combustion of significant amounts of sample. According to the invention first disclosed embodiment, it is actually possible to perform accurate and reliable analyses providing the absorption of the water present in the gases after passage through the reduction reactor only, thus avoiding the necessity to use another water trap that should forcibly be replaced every few dozens of analyses, with relevant costs and delays in the analysis times.

According to the invention second disclosed embodiment, it is possible to perform at the same time removal of $CO_2$ and $H_2O$, before the gases are fed to gas-chromatographic column. However, also in this case the thermal conductivity detector is preferably heated above water boiling point. The invention moreover concerns an apparatus for the determination of total nitrogen by means of flash dynamic combustion in a flow of helium or similar carrier gas, comprising a combustion reactor, a reduction reactor, gas drying means, means for $CO_2$ removal from the combustion gases, and a thermal conductivity detector, characterized in that it also comprises, upstream of said detector, a gas chromatographic column packed with a material suitable to separate nitrogen from methane possibly present within said combustion gases.

According to a preferred embodiment of the invention, the column for nitrogen separation is positioned downstream of the gas drying means and upstream of those for $CO_2$ removal, which are directly connected with said detector, that is provided with means for the control of its temperature.

According to another invention embodiment, $H_2O$ and $CO_2$ are both removed from combustion gases by means of a trap containing an hydrous soda lime (CaO+NaOH), provided upstream the gas-chromatographic column.

BRIEF DESCRIPTION OF THE DRAWINGS

The invention will be now described more in detail with reference to the accompanying drawings given by way of illustration and with no limiting purposes, where.

DETAILED DESCRIPTION

Figure 1:
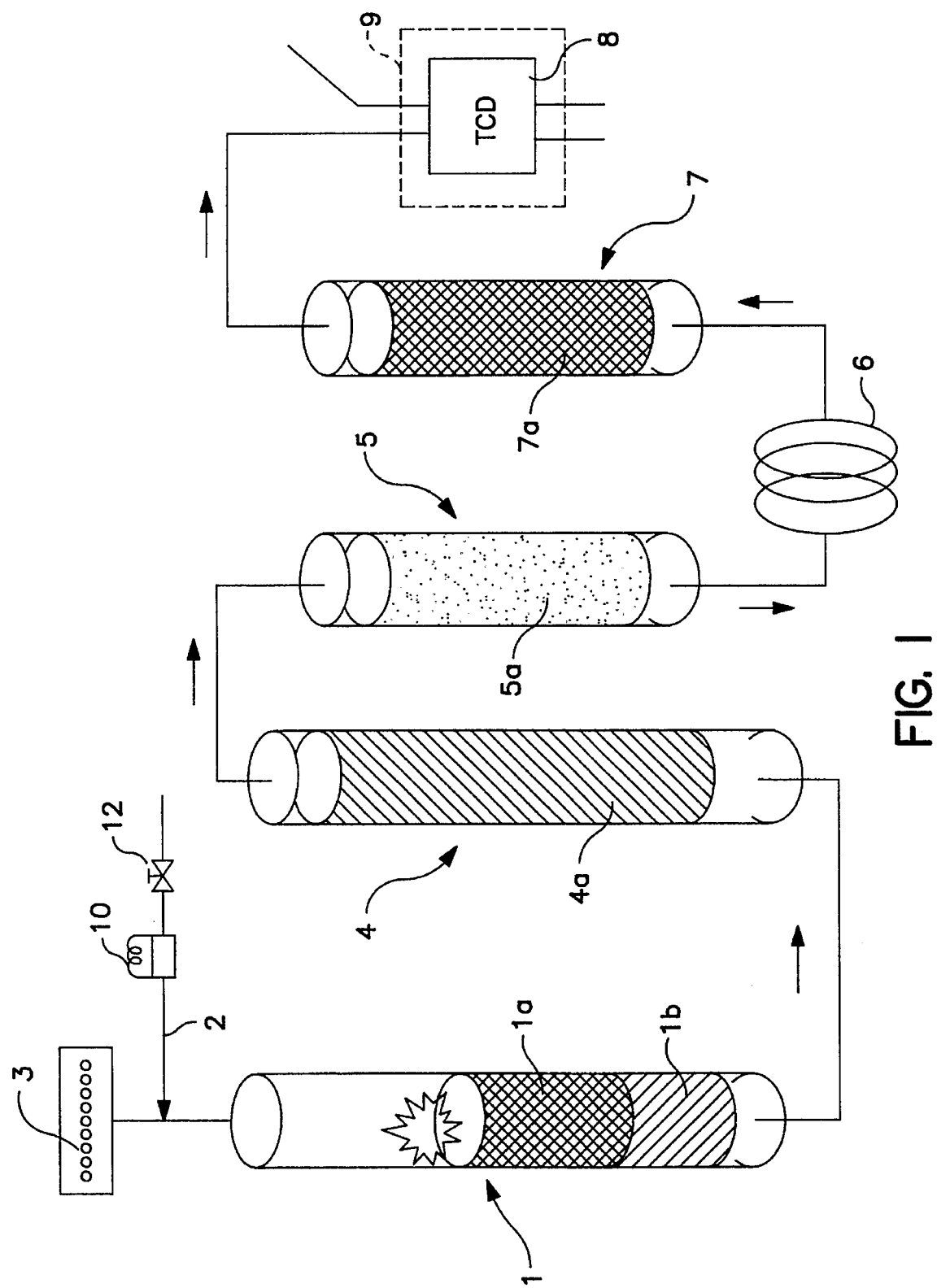
FIG. 1 is a schematic representation of an apparatus according to the invention.

With reference first of all to FIG. 1, the apparatus according to the invention comprises a combustion reactor 1, provided in a known way with means (not shown) for its heating and connected upstream with a line for feeding He or similar carrier gas, as well as a sampler 3 or equivalent means for feeding the samples to be analyzed into reactor 1.

The reactor 1 is known per se in this branch of the art and is provided with at least an oxidation catalyst of known type and preferably selected among Pt on alumina or similar supported noble metals possibly mixed to copper oxide (CuO); chrome oxide ($Cr_2O_3$), cobalt oxide ($Co_3O_4$), possibly supported, and mixtures thereof. Preferably, as shown in FIG. 1, two different layers of catalyst 1a and 1b are present.

The reactor 1 is connected at its outlet port, through a connecting line, to reduction reactor 4, known per se in the art, and containing metal Cu to perform the reduction of the combustion gases and to eliminate oxygen, possibly still present therein. A preferred material for this purpose consists in copper wires or in a mixture 4a of copper wires and quartz shavings. Also the reactor 4 is provided in a known way with means (not shown) for its own temperature control. The reduction reactor 4 is connected with means 5 to make anhydrous the mixture of gases coming from the reactor 4. According to the embodiment disclosed in FIG. 1, means 5 constitutes a trap for water and moisture only, of a type known in the art and commercially available, and consisting, for instance, of a container provided with $Mg(ClO_4)_2$, magnesium perchlorate, 5a.

Downstream trap 5, and connected thereto, there is provided a gaschromatographic column 6, to which gases coming out from the trap 5 are fed. As previously mentioned, the column is packed with a material suitable to separate nitrogen, previously formed in reactor 1 and in reduction reactor 4, from methane, $CH_4$, possibly formed by pyrolysis in reactor 1 during the flash dynamic combustion of the sample.

Column 6 must have relatively large dimensions and in any case such as not to cause excessive pneumatic resistance, since otherwise the correct sample combustion would be jeopardized. Preferred dimensions are: length within the range from 80 to 120 cm and internal diameter within the range from 4.0 to 10.0 mm.

Preferred materials to be used as packing suitable to perform $N_2/CH_4$ separation are for example activated carbon and molecular sieves of the Angstrom 5 type. Activated carbon is preferably used.

The outlet port of column 6 is connected to means 7, i.e. to means suitable for removing $CO_2$ from the combustion gases. Means 7 constitutes a so called trap for carbon dioxide, is known per se in the art, and comprises one or more compounds 7a for carbon dioxide absorption, such as ascarite, NaOH on alumina, commercial soda lime (CaO+ NaOH with 10–20% moisture content), and the like.

Means 7 is directly connected to thermal conductivity detector 8, known per se in the art and used in this field, which is provided with means 9 for temperature control such as for instance an oven or similar device.

Figure 4:
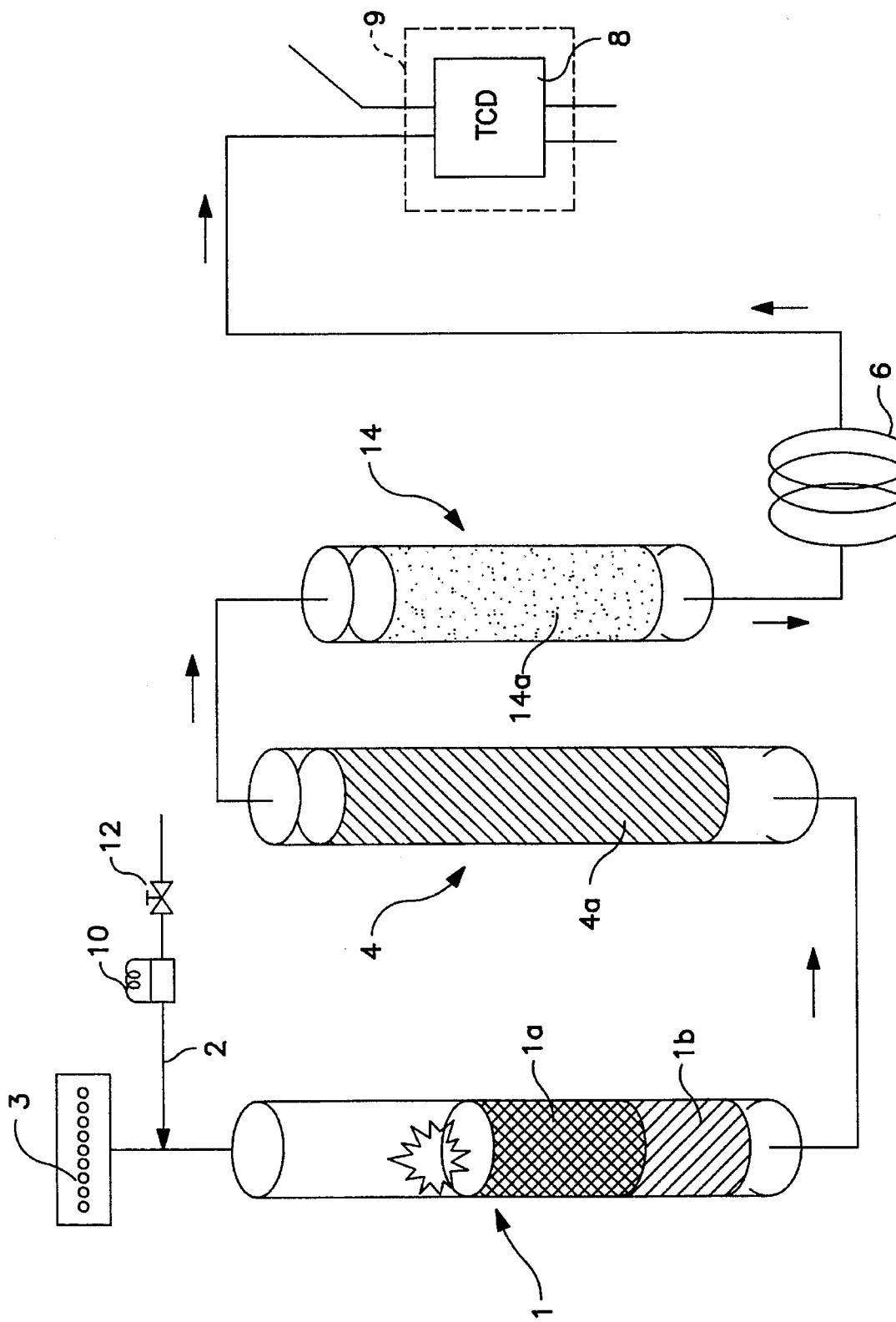
FIG. 4 is a schematic representation of another embodiment of the apparatus according to the invention.

According to another preferred embodiment disclosed in FIG. 4, downstream reduction reactor 4 and upstream column 6 there is provided means 14 where both $CO_2$ and $H_2O$ are trapped and removed from combustion gases. Means 14 contains anhydrous soda lime 14a, i.e. an anhydrous mixture of CaO and NaOH. Commercially available soda lime, on the contrary, contains 10 to 20% of moisture. It was found that while commercial soda lime is suitable only to absorb $CO_2$, anhydrous soda lime allows to absorb and remove from combustion gases both $CO_2$ and $H_2O$. In fact water is absorbed and activates soda lime to absorb also $CO_2$.

According to a further embodiment, another water trap (not shown) may be provided between means 14 and column 6 to ensure complete removal of water. This trap is known in the art and is preferably the same as trap means 5–5a previously disclosed with reference to FIG. 1 embodiment, or may be an anhydrone trap.

In both embodiments, to feed the reactor 1 with a quantity of oxygen sufficient for performing the analysis, the preferential embodiment of the invention provides on He feeding line 2 a loop 10, known per se in the art and controllably connectable with a feeding line of $O_2$ and with the line 2 itself.

Figure 2:
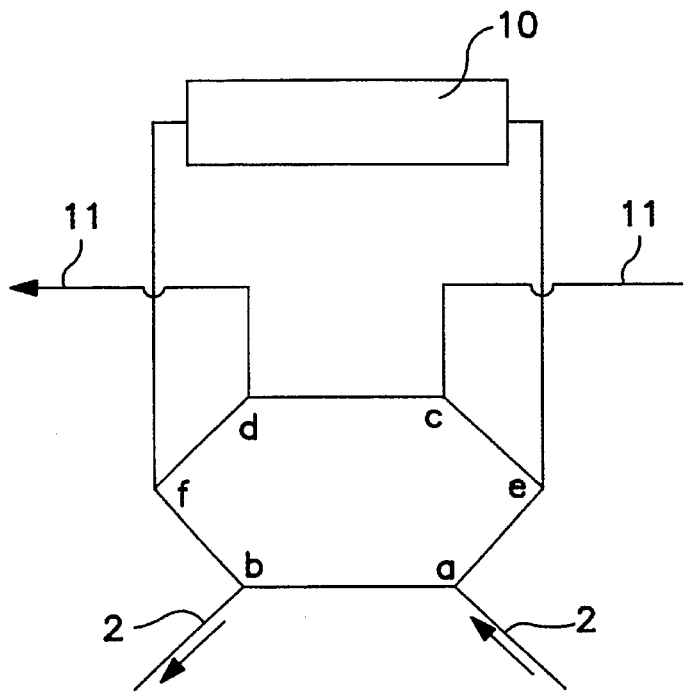
FIG. 2 is an enlarged schematic view of a detail of the equipment of FIG. 1.

FIG. 2 shows a schematic representation of the loop and of the relevant switching valve, where ports have been indicated with references a to f.

Loop 10 has a volume within the range from 10 to 200 ml, depending on the weight of the sample to be analyzed. For a sample weighing approximately 50–500 mg a 50 ml loop is used; pressure inside the loop will also be controlled as a function of the sample: in the previous case, a pressure equivalent to 150 relative KPa, and more generally, a pressure ranging between 60 and 200 relative KPa will be used.

As understandable from FIG. 2, when ports c–e, f–d and a–b are mutually connected, oxygen is loaded into the loop 10 through the line 11. When on the contrary ports a–e, f–b and c–d are connected to each other, oxygen passes into line 2 feeding helium to the equipment.

Upstream loop 10 there is also provided a flow rate regulator 12, that has the function of keeping He flow to the equipment constant during the whole analysis.

Figure 3:
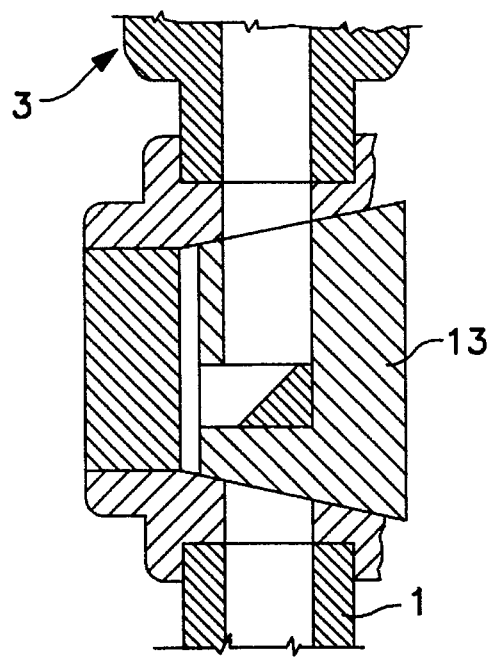
FIG. 3 is a partial section of a preferential sampler for the apparatus according to the invention.

The presence of regulator 12 is particularly useful since the high amounts of samples analyzed lead to increasing amounts of ashes to be deposited in the combustion reactor 1, with subsequent variation of its pneumatic resistance. As previously mentioned, the sample feeding takes place by means of the sampler 3. FIG. 3 shows in a schematic way a preferential embodiment of sampler, where instead of the known slide there is provided a septum 13 rotatable about its axis from a position where the sample is received (FIG. 3) to a position where the sample is fed to the combustion reactor 1. The second position is coaxial with the first one and corresponds to a rotation of the septum 13 by 180 degrees.

The aforementioned sampler is the object of a simultaneous patent application filed by the same applicant and entitled: "Device for feeding samples to elemental analysis apparatuses" (Italian Patent Application n. MI92A002035), to which reference is made herein for a more in-depth description and herein enclosed by reference.

The process according to the invention takes place according to the following stages.

First the sample is weighed and closed in a tin (or equivalent metal) capsule in a known way; then it is fed to the combustion reactor 1 where a flash dynamic combustion takes place in presence of oxygen that is fed, under pulse form, from loop 10 to reactor 1 simultaneously with the introduction of the sample into the reactor 1. In other words, oxygen present in the loop 10 is fed to the reactor 1 by appropriately switching ports a–f of the aforedescribed switching valve, so as to obtain a "pulsed" conveyance of oxygen and a flash dynamic combustion of the sample.

During this oxidation $N_2$, nitrogen oxides, $CO_2$, as well as water, $SO_2$, $Cl_2$, HCl and other gases are formed, depending on the content of the sample analyzed, and usually $CH_4$ as well. Methane generation frequently occurs, since the weight of the analyzed sample is relatively high and, differently from the known techniques, combustion is not carried out in high oxygen excess.

This stage is performed at a temperature within the range from 900 to 1100 degrees C., and preferably at a temperature of 1020 degrees C.

Halogens, hydrogen chloride and other halogen acids, sulfur dioxide, if present, are adsorbed on the oxidation catalysts and eventual residues on the $CO_2$ trap. The thus obtained gases coming from reactor 1 are conveyed to reduction reactor 2, where nitrogen oxides are reduced to $N_2$, and oxygen, if present, is fixed on copper as oxide. This stage is carried out at a temperature within the range from 500° to 800° C. and preferably at 700° C.

In FIG. 1 embodiment the reduced gases are then fed to means 5, where water present therein is removed, and afterwards conveyed to column 6, that performs the separation between $N_2$ and $CH_4$. When coming out from the column 6, the gases are fed to the $CO_2$ trap 7, so that carbon dioxide is removed and fixed on basic compounds 7a. These steps are carried out at a temperature substantially equal to room temperature.

As known, $CO_2$ removal results again in formation of water. To avoid problems because of the water present again in the gases to be analyzed, according to first embodiment of FIG. 1, there is no water elimination by means of further traps, but the detector 8 is thermostated at a temperature at least equal to that of water vaporization in said gases fed to the detector, and the gases coming out from trap 7 are fed to the thus heated detector together with water and moisture present in said gases. The detection temperature is generally within the range from 100° to 150° C. and is preferably 120° C.

In this way the operation of further eliminating formed water is avoided and simultaneously a high linearity of the performed analyses and a good sensitivity of the detector are obtained.

Figure 5:
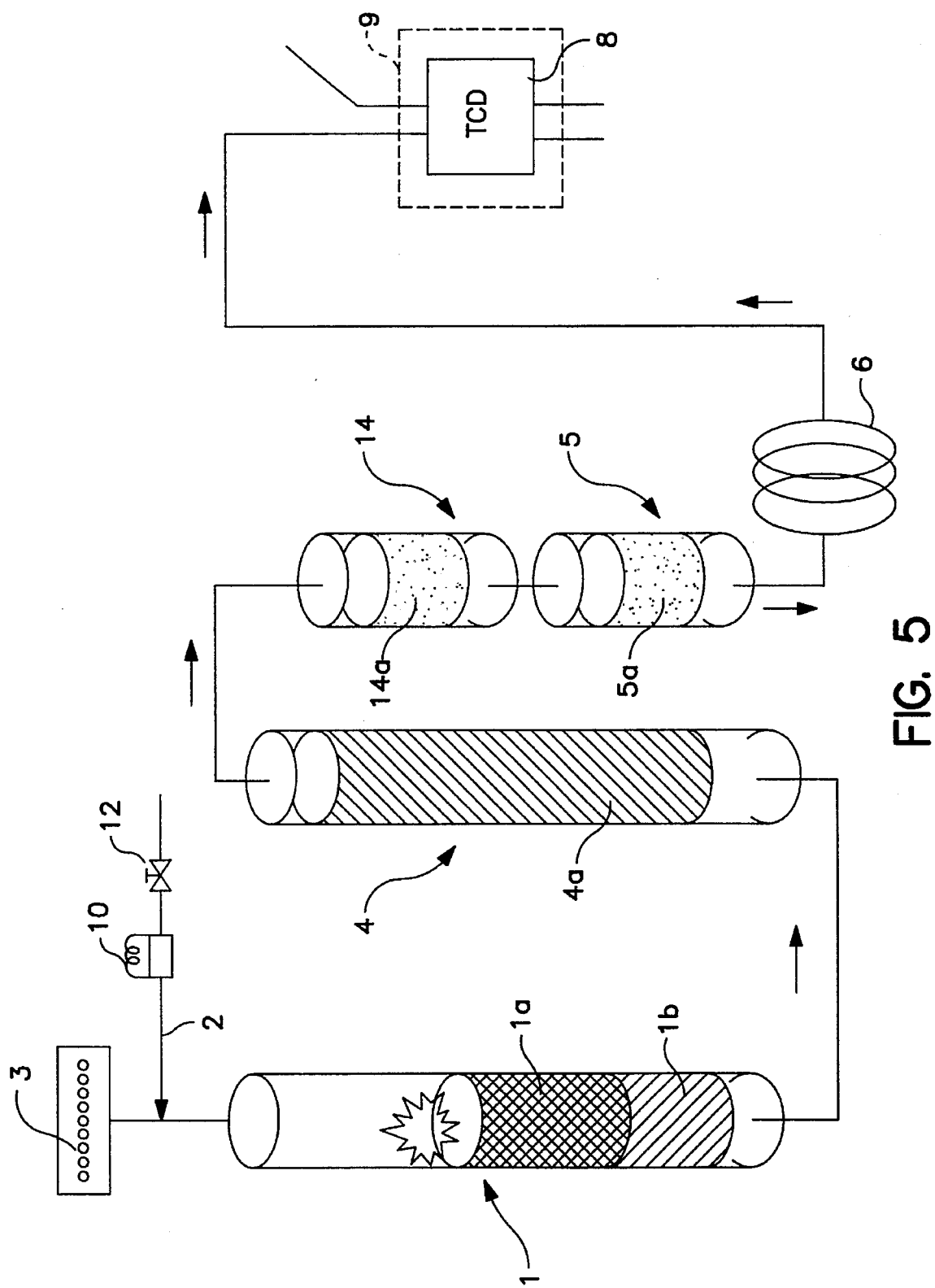
FIG. 5 is a schematic representation of a further embodiment of the apparatus according to the invention.

In FIG. 4 and FIG. 5 embodiments, gases coming out from reactor 4 are fed to trap means 14 were both $CO_2$ and water are removed therefrom. Optionally, gases exiting trap means 14 may be passed through a further water trap (not shown) in FIG. 4 such as means 5 disclosed with reference to FIG. 1 and FIG. 5 embodiments. After $CH_4/N_2$ separation in column 6, gases are fed to TCD detector 8, which is preferably kept at the same conditions above disclosed with reference to FIG. 1 embodiment.

The following table reports the results obtained from the analyses of 16 different samples: for each of them 10 analyses were performed.

The test conditions used were as follows: temperature of flash combustion reactor 1020° C.; temperature of reduction reactor 700° C.; $O_2$ loop : 50 ml at 150 relative KPa; gases dried on anhydron; column packed with activated C; $CO_2$ removed on soda lime; TCD detector temperature 120 degrees C.

TABLE I

| COMPOUND | QUANTITY (mg) | AVERAGE N. % | STAND. DEV. | REL. STAND. DEV. % |
|---|---|---|---|---|
| FLOUR | 100–200 | 1.94 | 0.008 | 0.405 |
| CORN | 100–200 | 1.22 | 0.011 | 0.917 |
| RICE | 100–180 | 1.10 | 0.009 | 0.831 |
| SOY | 100–150 | 6.99 | 0.037 | 0.529 |
| BRAN | 100–150 | 2.27 | 0.018 | 0.807 |
| YEAST | 100–150 | 7.87 | 0.043 | 0.544 |
| FORAGE | 100–130 | 1.44 | 0.016 | 1.076 |
| PASTA | 130–250 | 2.20 | 0.009 | 0.431 |
| MILK | 100–250 | 0.60 | 0.007 | 1.224 |
| POWDER MILK | 100–150 | 1.84 | 0.008 | 0.460 |

TABLE I-continued

| COMPOUND | QUANTITY (mg) | AVERAGE N. % | STAND. DEV. | REL. STAND. DEV. % |
|---|---|---|---|---|
| CHEESE | 100–150 | 3.45 | 0.015 | 0.449 |
| CHOCOLATE | 100–150 | 1.20 | 0.007 | 0.615 |
| COCOA | 100–150 | 4.35 | 0.031 | 0.708 |
| BABIES FOOD | 200–400 | 1.26 | 0.010 | 0.832 |
| OAT-WHEAT MIXTURE | 100–200 | 2.87 | 0.020 | 0.705 |
| DL-METHIONINE | 40–80 | 9.40 | 0.027 | 0.287 |

We claim:

1. A process for determining the nitrogen content of a sample, comprising the steps of:
   (a) combusting said sample in a combustion reactor in the presence of oxygen, which oxygen is introduced into the combustion reactor in pulse form; using a loop, simultaneously with a sample, the volume of oxygen introduced being of from 10 to 200 ml per pulse at a pressure of from 80 to 200 KPa,
   (b) reducing the resulting combustion gasses by flowing them in a flow of a noble carrier gas through a Cu-containing reduction reactor;
   (c) performing the steps of (i) drying the reduced gases in a water trap, (ii) flowing the reduced gases through a gas-chromatographic column in order to carry out a gas chromatographic separation of $N_2$ from $CH_4$ possibly present within the reduced gases, which gas chromatographic column is packed with a material suitable for separating $N_2$ from $CH_4$, and (iii) removing $CO_2$ from the reduced gases using a $CO_2$ trap, with the proviso that step (i) immediately precedes step (ii); and
   (d) analyzing the resulting gases using a means for detecting thermal conductivity, so as to thereby determine the nitrogen content of the sample.

2. The process according to claim 1, wherein said separation on the gas-chromatographic column is carried out after the gases are dried and before $CO_2$ removal; and the gases obtained after $CO_2$ removal are directly fed to the means for detecting thermal conductivity, said means being kept at a temperature at least equal to that allowing the full vaporization of the water present in the gases resulting from the $CO_2$ removal step.

3. The process according to claim 1, wherein the water trapping and $CO_2$ removal steps are carried out before the gas-chromatographic separation step.

4. The process according to claim 1, wherein the flow rate of the noble carrier gas is kept constant.

5. The process according to claim 1, wherein the combustion reactor is kept at a temperature of from 900 to 1100 degrees C., the reduction reactor is kept at a temperature of from 500 to 800 degrees C.; steps (i)–(iii) are carried out at room temperature; and the means for detecting thermal conductivity is kept at a temperature of from 100 to 150 degrees C.

6. The process according to claim 1, wherein a sample weighing between 20 and 500 mg is analyzed in He flow, the combustion is carried out at 1020 degrees C. with an amount of $O_2$ equal to 50 ml at 150 KPa, the reduction is carried out at 700 degrees C., and the detection is carried out at 120 degrees C.

7. An apparatus for determining the total nitrogen content of a sample by means of flash combustion comprising:
   (a) a combustion reactor for producing combustion gases from said sample having a noble carrier gas flowing therethrough,
   (b) means for simultaneously introducing oxygen and a sample into the combustion reactor, wherein the oxygen is introduced in pulse form using a loop having a volume of from 10 to 200 ml per pulse and a pressure of from 80 to 200 KPa,
   (c) a reduction reactor connected downstream of the combustion reactor,
   (d) means for trapping water connected downstream of the reduction reactor,
   (e) a gas chromatographic column packed with a material suitable for separating nitrogen gas from methane present within said combustion gases connected directly downstream of the means for trapping water,
   (f) a thermal conductivity detector connected downstream of the chromatographic column, and
   (g) means for removing $CO_2$ from the combustion and carrier gases provided between the reduction reactor and the thermal conductivity detector with the proviso that the means for removing $CO_2$ cannot be located between the means for removing water and the gas chromatographic column.

8. The apparatus according to claim 7, wherein said means for removing $CO_2$ is positioned downstream of said gas chromatographic column and said means for removing $CO_2$ is directly connected to said thermoconductivity detecter, said thermal conductivity detector being provided with a means for controlling its temperature.

9. The apparatus according to claim 8, wherein said means for trapping water and said means for removing $CO_2$ both consist essentially of anhydrous soda lime.

10. The apparatus according to claim 9, further comprising a second means for trapping water provided between said means for trapping water and means for removing $CO_2$.

11. The apparatus according to claim 7, wherein said means for trapping water and said means for removing $CO_2$ are both upstream of said gas-chromatographic column.

12. The apparatus according to claim 7, wherein said gas-chromatographic column is packed with activated carbon.

13. The apparatus according to claim 7, wherein said gas-chromatographic column has a length of from 80 to 120 cm and an internal diameter of from 4.0 to 10.0 mm.

14. The apparatus according to claim 7, further comprising a means for regulating flow rate to keep the noble carrier gas flow rate constant.

15. The apparatus according to claim 7, further comprising a sampler having a truncated cone septum rotatable about its axis from a position in which the sample is received to a position in which said sample is released into the combustion reactor.

* * * * *